(12) United States Patent
Marco et al.

(10) Patent No.: US 11,478,585 B2
(45) Date of Patent: Oct. 25, 2022

(54) SYRINGE GASKET

(71) Applicant: SUMITOMO RUBBER INDUSTRIES, LTD., Kobe (JP)

(72) Inventors: Pederiva Marco, Merenschwand (CH); Protti Roberto, Merenschwand (CH)

(73) Assignee: SUMITOMO RUBBER INDUSTRIES, LTD., Kobe (JP)

( * ) Notice: Subject to any disclaimer, the term of this patent is extended or adjusted under 35 U.S.C. 154(b) by 408 days.

(21) Appl. No.: 16/637,190

(22) PCT Filed: May 29, 2018

(86) PCT No.: PCT/JP2018/020545
§ 371 (c)(1),
(2) Date: Feb. 6, 2020

(87) PCT Pub. No.: WO2019/031028
PCT Pub. Date: Feb. 14, 2019

(65) Prior Publication Data
US 2020/0368444 A1    Nov. 26, 2020

(30) Foreign Application Priority Data
Aug. 9, 2017    (JP) .............................. JP2017-154139

(51) Int. Cl.
*B29C 39/10*    (2006.01)
*A61M 5/315*    (2006.01)
(Continued)

(52) U.S. Cl.
CPC ......... *A61M 5/31513* (2013.01); *B29C 39/10* (2013.01); *B29C 51/12* (2013.01);
(Continued)

(58) Field of Classification Search
CPC ............................... B29C 39/10; B29C 51/12
See application file for complete search history.

(56) References Cited

U.S. PATENT DOCUMENTS 7,727,202 B2 *   6/2010   Kirchhofer ....... A61M 5/31513
                                                                 604/218
9,452,264 B2 *   9/2016   Maeda ................... B29C 43/184
(Continued)

FOREIGN PATENT DOCUMENTS

JP    2001-190667 A    7/2001
JP    2005-13315 A    1/2005
(Continued)

OTHER PUBLICATIONS

International Search Report issued in PCT/JP2018/020545 (PCT/ISA/210), dated Jan. 10, 2018.
(Continued)

*Primary Examiner* — Edmund H Lee
(74) *Attorney, Agent, or Firm* — Birch, Stewart, Kolasch & Birch, LLP (57) ABSTRACT

Provided is a syringe gasket including a first member, and a second member connected to the first member and coupled to a plunger rod of a syringe. The first member includes a top face contacting with the liquid, and a first side circumferential face that faces an inner circumferential face of a barrel of the syringe. The first side circumferential face has, at an end portion thereof close to the second member, a ring-like trimmed face. An inert film is laminated on the top face and the portion of the first side circumferential face other than the ring-like trimmed face. The second member includes a second side circumferential face that faces the inner circumferential face of the barrel, and a ring-like protruding portion that projects outward in the radial direction from the second side circumferential face. The ring-like protruding portion at least partially covers the ring-like trimmed face.

13 Claims, 6 Drawing Sheets

(51) Int. Cl.
*B29C 51/12* (2006.01)
*B29K 21/00* (2006.01)
*B29L 31/26* (2006.01)

(52) U.S. Cl.
CPC . *A61M 2205/0238* (2013.01); *A61M 2207/00* (2013.01); *B29K 2021/003* (2013.01); *B29K 2995/0058* (2013.01); *B29L 2031/265* (2013.01)

(56) References Cited

U.S. PATENT DOCUMENTS

| | | | | |
|---|---|---|---|---|
| 10,058,658 | B1* | 8/2018 | Voytilla | A61M 5/31515 |
| 10,456,527 | B2* | 10/2019 | Yotsutsuji | A61M 5/31513 |
| 2004/0084852 | A1 | 5/2004 | Tachikawa et al. | |
| 2007/0219508 | A1* | 9/2007 | Bisegna | A61M 5/31513 |
| | | | | 604/218 |
| 2013/0053786 | A1* | 2/2013 | Maeda | B29C 33/3842 |
| | | | | 425/112 |
| 2014/0228774 | A1* | 8/2014 | Maeda | B29C 43/184 |
| | | | | 604/222 |
| 2014/0288508 | A1* | 9/2014 | Iwano | A61L 31/10 |
| | | | | 604/222 |
| 2016/0101239 | A1* | 4/2016 | Ishida | A61M 5/31513 |
| | | | | 604/222 |
| 2017/0232202 | A1* | 8/2017 | Yotsutsuji | A61L 31/048 |
| | | | | 604/272 |
| 2017/0368264 | A1* | 12/2017 | Fournier | A61L 31/048 |
| 2018/0200450 | A1 | 7/2018 | Lilly et al. | |

FOREIGN PATENT DOCUMENTS

| | | |
|---|---|---|
| JP | 2016-77354 A | 5/2016 |
| JP | 5947823 B2 | 7/2016 |
| WO | WO 02/22192 A1 | 3/2002 |
| WO | WO 2016/120565 A1 | 8/2016 |
| WO | WO 2017/011599 A1 | 1/2017 |

OTHER PUBLICATIONS

Written Opinion of International Searching Authority issued in PCT/JP2018/020545 (PCT/ISA/237), dated Jan. 10, 2018.
Extended European Search Report for European Application No. 18843196.9, dated Mar. 16, 2021.

* cited by examiner

SYRINGE GASKET

TECHNICAL FIELD

The present invention relates to a gasket for a syringe, and particularly relates to a gasket for a prefilled syringe.

BACKGROUND ART

Gaskets that slide inside a barrel by being pushed with a plunger rod while maintaining liquid tightness so as to prevent leakage of a liquid such as a medical fluid inside the barrel are used for syringes (injectors). Such gaskets are made of an elastic material such as rubber or a thermoplastic elastomer in order to maintain liquid tightness by being in close contact, without a gap, with the inner circumferential face of the barrel of syringes. Incidentally, in recent years, prefilled syringes that have been filled with a liquid in advance are becoming widely used in order to prevent mix-ups of medical fluids and the like. Especially in the case of such prefilled syringes, when a gasket and a liquid are in contact with each other for a long period of time, particles of components of a material of which the gasket is made are highly likely to elute into the liquid, thereby contaminating or deteriorating the liquid. Accordingly, conventional syringe gaskets are required not only to be slidable and liquid-tight but also to be liquid-resistant so as not to contaminate or deteriorate a liquid even when stored in contact with the liquid for a long period of time.

Patent Literatures 1 and 2 disclose syringe gaskets whose top face and side circumferential face are coated with an inert film made of a resin that is inert to a liquid. Such gaskets are molded by placing an inert film and a rubber sheet in an overlapping manner in a mold and then performing heating compression or the like. After the molding, the rubber sheet is punched to obtain gaskets. According to Patent Literature 2, punching is performed while causing a pulling force to act on the rubber sheet (which may be referred to as an "undercut method"). Accordingly, the rubber on the cut face is prevented from bulging out from the outer circumference of the side circumferential face of the gasket.

CITATION LIST

Patent Literatures

Patent Literature 1: JP 2016-77354A
Patent Literature 2: Japanese Patent No. 5947823

SUMMARY OF INVENTION

Technical Problem

In the case of punching a rubber sheet from the top face side without applying a pulling force to the rubber sheet, a punching blade may accidentally come into contact with the inert film laminated on the top face or the side circumferential face due to an error in the positioning of the punching blade relative to the rubber sheet or the like, resulting in damage to or peeling off of the inert film. On the other hand, in the undercut method, punching is performed while the rubber sheet that corresponds to the bottom of the molded portion is stretched apart, and thus the punching blade does not come into contact with the inert film, so that the above-described problems are not likely to occur.

However, it may be difficult to control the pulling force that is to act on the rubber sheet in the undercut method. Since the gasket returns to its original shape due to the internal stress of the rubber when the pulling force is canceled after the cutting, according to the undercut method, variations or errors may appear in the dimensions of the gasket around the cut portion. If variations or errors appear in the outer circumferential dimensions of the gasket, the gasket cannot be in close contact with the inner wall of the syringe with a uniform force thereagainst. Accordingly, the gasket may wobble inside the barrel, and the liquid may come into contact with a portion of the gasket not coated with the inert film, and the liquid tightness may be impaired.

It is an object of the present invention to improve the liquid tightness of a liquid-resistant syringe gasket.

Solution to Problem

A first aspect of the present invention is directed to a syringe gasket configured to be coupled to a plunger rod of a syringe, and to slide inside a barrel of the syringe by being pushed with the plunger rod, including: a first member configured to be inserted into the barrel, and to be in contact with a liquid accommodated in the barrel; and a second member configured to be inserted into the barrel, and to be coupled to the plunger rod, the second member being connected to the first member. The first member includes: a top face configured to be in contact with the liquid; and a first side circumferential face that is continuous with an outer circumferential edge of the top face, and configured to face an inner circumferential face of the barrel. The first side circumferential face has, at an end portion thereof close to the second member, a ring-like trimmed face, and the ring-like trimmed face is recessed to be closer to the inner side in a radial direction than the portion of the first side circumferential face other than the ring-like trimmed face. An inert film is laminated on the top face and the portion of the first side circumferential face other than the ring-like trimmed face. The second member includes: a second side circumferential face configured to face the inner circumferential face of the barrel; and a ring-like protruding portion that extends in a circumferential direction on the second side circumferential face, projects outward in the radial direction from the second side circumferential face, and is configured to be contact with the inner circumferential face of the barrel when the second member is inserted into the barrel. The ring-like protruding portion at least partially covers the ring-like trimmed face from the outer side in the radial direction.

A second aspect of the present invention is directed to the syringe gasket according to the first aspect, wherein the ring-like protruding portion covers the entire ring-like trimmed face from the outer side in the radial direction.

A third aspect of the present invention is directed to the syringe gasket according to the first or second aspect, wherein the first member and the second member are made of a rubber or a thermoplastic elastomer.

A fourth aspect of the present invention is directed to the syringe gasket according to any one of the first to third aspects, wherein the top face has a convex portion projecting toward a space in which the liquid is accommodated in the barrel.

A fifth aspect of the present invention is directed to the syringe gasket according to any one of the first to fourth aspects, wherein the top face has, at an outer circumferential portion thereof, an inclined face that is inclined toward the second member as being closer to the outer side in the radial direction.

A sixth aspect of the present invention is directed to the syringe gasket according to the fifth aspect, wherein an angle formed by the portion of the first side circumferential face other than the ring-like trimmed face and the inclined face is 90° or more and 110° or less.

A seventh aspect of the present invention is directed to the syringe gasket according to any one of the first to sixth aspects, wherein the inert film is made of a material selected from the group consisting of tetrafluoroethylene-ethylene copolymer, modified tetrafluoroethylene-ethylene copolymer, and polychlorotrifluoroethylene.

An eighth aspect of the present invention is directed to a method for producing a syringe gasket configured to be coupled to a plunger rod of a syringe, and to slide inside a barrel of the syringe by being pushed with the plunger rod, including the following steps:

(1) placing in an overlapping manner a first material that is a material of a rubber or a thermoplastic elastomer and an inert film, in a cavity of a first mold, such that the inert film is positioned on the deeper side;

(2) molding a first sheet including a layer of the inert film and a layer of the first material, by molding the first material and the inert film together in the cavity of the first mold;

(3) punching a predetermined portion of the first sheet from the inert film side while causing a pulling force to act on the first sheet, thereby obtaining a first member in which the inert film is laminated on a top face and a side circumferential face thereof and a ring-like trimmed face is formed on a bottom portion opposite to the top face;

(4) placing the first member in a cavity of a second mold such that the top face is positioned on the deeper side;

(5) molding a second member connected to the bottom portion of the first member, by pouring a second material that is a material of a rubber or a thermoplastic elastomer on the first member in the cavity of the second mold in which the first member has been placed; and (6) removing the syringe gasket including the first member and the second member from the second mold.

The step (6) includes pouring the second material such that the second material is in contact with the ring-like trimmed face of the first member, and a ring-like protruding portion that at least partially covers the ring-like trimmed face is formed.

Advantageous Effects of Invention

The present invention provides a syringe gasket that is liquid-resistant and excellent in terms of liquid tightness.

DESCRIPTION OF EMBODIMENTS

Hereinafter, a syringe gasket according to an embodiment of the present invention will be described with reference to the drawings.

1. Configuration of Syringe Gasket

Figure 1:
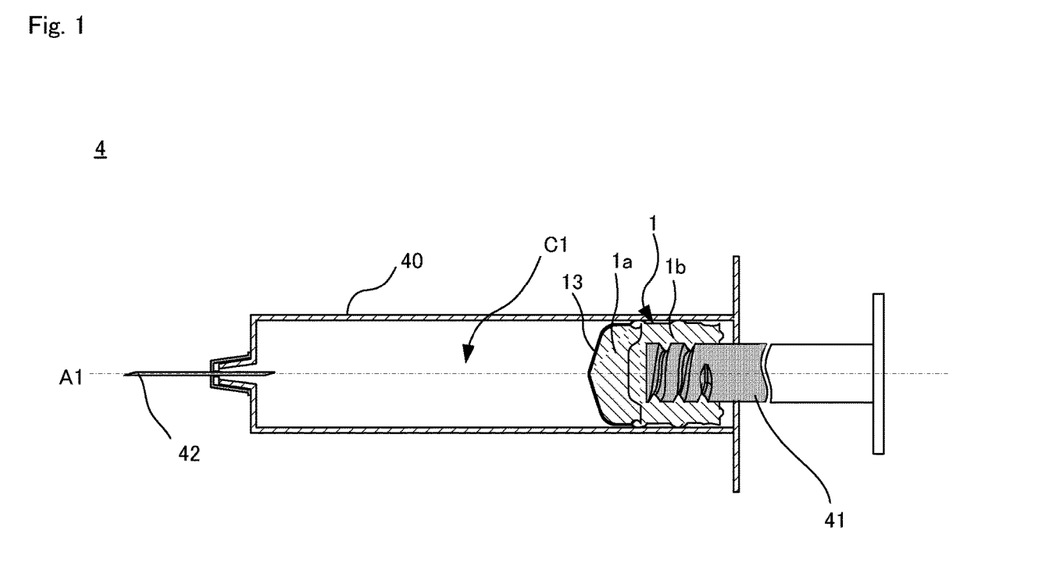
FIG. 1 is a cross-sectional view of a syringe using a syringe gasket according to an embodiment of the present invention.
Figure 2:
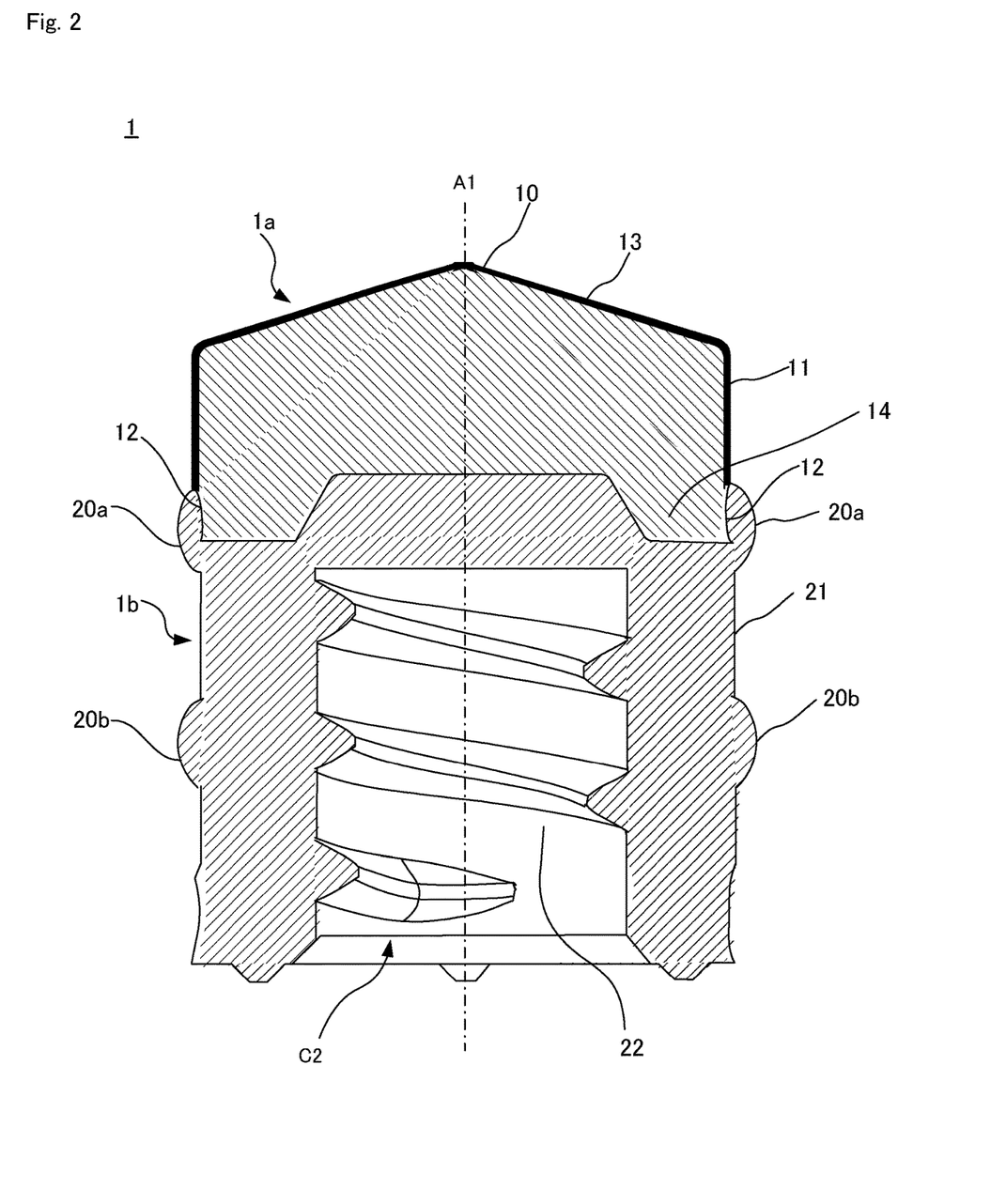
FIG. 2 is a cross-sectional view of the syringe gasket according to an embodiment of the present invention.

FIG. 1 is a cross-sectional view of a syringe 4 using a syringe gasket (hereinafter, may simply be referred to as a "gasket") 1 according to this embodiment, and FIG. 2 is a cross-sectional view of the gasket 1. The gasket 1 is attached to the front end of a plunger rod (hereinafter, may simply be referred to as a "rod") 41 of the syringe 4, and inserted into a barrel 40 of the syringe 4 together with the rod 41. Accordingly, in the barrel 40, a space (hereinafter, referred to as an "accommodation space") C1 defined by the inner circumferential face of the barrel 40 and the gasket 1, and the accommodation space C1 is filled with a liquid. The gasket 1 slides inside the barrel 40 in accordance with the rod 41 being pushed, and is used to push the liquid inside the accommodation space C1 toward an injector needle 42. Note that the liquid herein is typically a medical fluid. The syringe 4 according to this embodiment is a prefilled syringe, and the accommodation space C1 accommodates the liquid in advance before use of the syringe 4.

The gasket 1 includes a first member 1a and a second member 1b, and the members 1a and 1b are inseparably connected to each other in one piece. The first member 1a has a top face 10, and the top face 10 is in contact with the liquid inside the accommodation space C1. The second member 1b is connected to a bottom portion 14 of the first member 1a opposite to the top face 10 in the direction in which a central axis A1 extends. The central axis A1 refers to a central axis direction of the barrel 40 substantially in the shape of a cylinder as shown in FIGS. 1 and 2, and the direction in which the central axis A1 extends matches the direction in which the gasket 1 slides inside the barrel 40. In the description below, the position of the central axis A1 may be referred to when describing not only the syringe 4 but also the structure of each portion in the gasket 1, but, in this case, the state in which the gasket 1 is inserted in the barrel 40 is taken as a reference. Furthermore, also when describing the positional relationship between the barrel 40 and the gasket 1, the state in which the gasket 1 is inserted in the barrel 40 is taken as a reference. In this embodiment, the inner circumferential face of the barrel 40 is configured such that its cross-section that is orthogonal to the central axis A1 is substantially in the shape of a circle, and the gasket 1, and the first member 1a and the second member 1b constituting the gasket 1 are configured such that their cross-sections that are orthogonal to the central axis A1 are substantially in the shape of a circle.

The first member 1a and the second member 1b are made of an elastic material, and typically made of rubber or a thermoplastic elastomer. More specifically, the first member 1a and the second member 1b may be made of butyl rubber, isoprene rubber, butadiene rubber, halogenated butyl rubber, ethylene-propylene terpolymer, silicone rubber, or the like, but there is no limitation to these examples. The first member 1a and the second member 1b may be made of the same material or may be made of different materials.

The first member 1a has a first side circumferential face 11 that is continuous with the outer circumferential edge of the top face 10 and faces the inner circumferential face of the barrel 40. When the first member 1a is inserted into the barrel 40, the inner circumferential face of the barrel 40 and the first side circumferential face 11 face each other substantially in parallel. The first side circumferential face 11 has, at an end portion thereof close to the second member 1b in the direction in which the central axis A1 extends, a ring-like trimmed face 12. The ring-like trimmed face 12 is recessed to be further inward in the radial direction than the other portions in the first side circumferential face 11, and cannot be seen in plan view from the side of the top face 10 of the first member 1a. The radial direction herein is defined using the central axis A1 as a reference, unless otherwise described. An inert film 13 that does not react with the liquid is laminated on the top face 10 and the first side circumferential face 11. Note that the inert film 13 is not laminated on the ring-like trimmed face 12. Accordingly, the entire ring-like trimmed face 12 is covered by the second member 1b from the outer side in the radial direction as described later, but there is no inert film 13 between the ring-like trimmed face 12 and the second member 1b. Hereinafter, a region in which the inert film 13 is laminated is referred to as an inert region.

The portion of the first side circumferential face 11 other than the ring-like trimmed face 12 is in contact with the inner circumferential face of the barrel 40 or faces the inner circumferential face of the barrel 40 with a slight gap interposed therebetween. Accordingly, the liquid is substantially confined within the accommodation space C1 between the barrel 40 and the top face 10, so that the liquid is in contact with the top face 10, but is not in contact with or is barely in contact with the other portions of the gasket 1. Thus, the liquid is mainly in contact with only the top face 10 coated with the inert film 13, and thus a situation is prevented in which particles of components of a material of which the first member 1a and the second member 1b are made elute into the liquid inside the accommodation space C1, thereby contaminating or deteriorating the liquid. As a result, the gasket 1 has high liquid resistance, and has high medical fluid resistance in the case where the liquid is a medical fluid.

As described above, in the gasket 1, not only the top face 10 that is in contact with the liquid but also the portion of the first side circumferential face 11 other than the ring-like trimmed face 12, the portion not being in contact with the liquid or barely being in contact with the liquid, is coated with the inert film 13. The reason for this is that, in the case of coating only the top face 10, there may be a region not coated with the inert film 13 near the outer circumferential edge of the top face 10 due to production errors. Thus, the top face 10 can be reliably coated with the inert film 13 by laminating the inert film 13 not only on the top face 10 but also on a region of the first side circumferential face 11 near the outer circumferential edge of the top face 10.

The inert film 13 is typically made of a fluorine resin or an olefin-based resin. More specifically, the inert film 13 is made of tetrafluoroethylene-ethylene copolymer (ETFE), a modified tetrafluoroethylene-ethylene copolymer, polytetrafluoroethylene (PTFE), polychlorotrifluoroethylene (PCTFE), or the like, but there is no limitation to these materials.

Figure 3A:
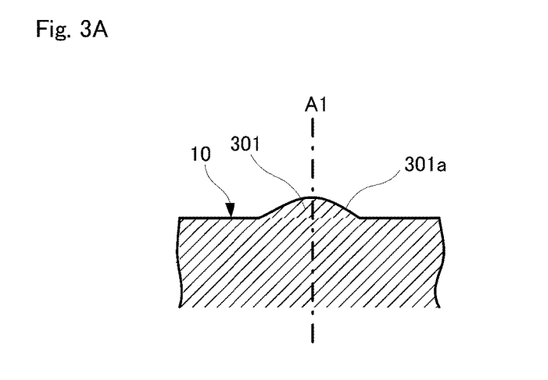
FIG. 3A is a cross-sectional view showing the shapes of top faces of the syringe gasket according to another embodiment of the present invention.
Figure 3B:
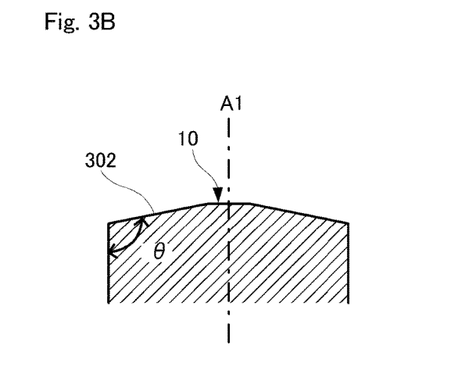
FIG. 3B is a cross-sectional view showing the shapes of top faces of the syringe gasket according to yet another embodiment of the present invention.
Figure 3C:
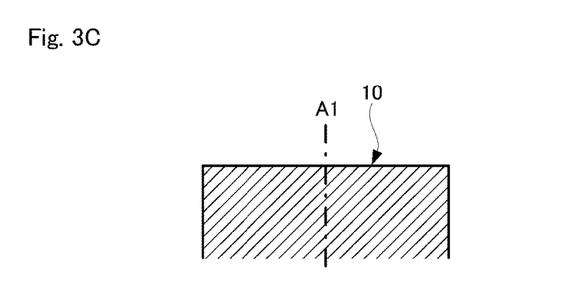
FIG. 3C is a cross-sectional view showing the shapes of top faces of the syringe gasket according to still another embodiment of the present invention.

The shape of the top face 10 is not limited to that shown in FIG. 2. For example, as shown in FIG. 3A, the top face 10 may have a convex portion 301 projecting toward the accommodation space C1 of the liquid. At this time, the convex portion 301 may have an inclined face 301a that is inclined from the position of the central axis A1 toward the second member 1b as it approaches the outer side in the radial direction, and the portion of the top face 10 other than the inclined face 301a may be a flat face that is orthogonal to the central axis A1. Furthermore, although not shown, the top face 10 may have a plurality of steps of inclined faces. Also, as shown in FIG. 3B, the top face 10 may have a shape in which the circumferential portion of the top face 10 has an inclined face 302 that is inclined toward the second member 1b as it approaches the outer side in the radial direction (the circumferential portion of the top face 10 is chamfered along the circumferential direction). At this time, the portion of the top face 10 other than the inclined face 302 may be a flat face that is orthogonal to the central axis A1. At this time, an angle $\theta$ formed by the first side circumferential face 11 other than the ring-like trimmed face 12 and the inclined face 302 is preferably 90° or more and 110° or less. Also, as shown in FIG. 3C, the entire top face 10 may be a flat face that is orthogonal to the central axis A1.

The second member 1b has a second side circumferential face 21 that faces the inner circumferential face of the barrel 40, and two ring-like protruding portions 20a and 20b that stand upright on the second side circumferential face 21. When the second member 1b is inserted into the barrel 40, the second side circumferential face 21 faces the inner circumferential face of the barrel 40 substantially in parallel. The ring-like protruding portions 20a and 20b are arranged on the second side circumferential face 21 with a predetermined gap interposed therebetween in the direction in which the central axis A1 extends, and the ring-like protruding portion 20a is arranged closer to the accommodation space C1 than the ring-like protruding portion 20b is. In this embodiment, the first side circumferential face 11 of the first member 1a and the second side circumferential face 21 of the second member 1b are at substantially the same distance from the central axis A1. Accordingly, the ring-like protruding portions 20a and 20b protrude, in the radial direction, past not only the second side circumferential face 21 but also the first side circumferential face 11. Furthermore, the ring-like protruding portions 20a and 20b have substantially the same height using the second side circumferential face 21 as a reference. Thus, when the gasket 1 is inserted into the barrel 40, the ring-like protruding portions 20a and 20b both come into contact with the inner circumferential face of the barrel 40, and, at this time, the ring-like protruding portions 20a and 20b are in close contact, without a gap, with the inner circumferential face of the barrel 40 due to the elasticity of the material thereof.

The ring-like protruding portions 20a and 20b extend on the second side circumferential face 21 throughout the circumferential direction. The circumferential direction herein is defined using the central axis A1 as a reference. As described above, the liquid inside the accommodation space C1 is tightly confined with the ring-like protruding portion 20a that is in close contact with the barrel 40, and does not leak out of the gasket 1. Furthermore, the ring-like protruding portions 20a and 20b support the gasket 1 such that the central axis of the gasket 1 matches the central axis A1 of the barrel 40. Accordingly, in this embodiment, the central axis of the gasket 1 does not deviate or shift from the central axis A1 of the barrel 40, and, furthermore, the liquid tightness of the barrel 40 is maintained.

As shown in FIG. 2, in this embodiment, the ring-like protruding portion 20a covers the entire ring-like trimmed face 12 from the outer side in the radial direction. Thus, the ring-like protruding portion 20a can firmly support the bottom portion 14 of the first member 1a. As a result, not only the second member 1b having the ring-like protruding portions 20a and 20b that are in close contact with the inner circumferential face of the barrel 40 but also the first member 1a can be firmly supported with the ring-like protruding portion 20a inside the barrel 40, and thus the gasket can reliably slide inside the barrel 40. Accordingly, the central axis of the first member 1a is not likely to deviate from the central axis A1 of the barrel 40, and thus the liquid tightness is further improved. Note that the ring-like protruding portion 20a does not necessarily have to cover the entire ring-like trimmed face 12 from the outer side in the radial direction. In order to firmly support the first member 1a, the ring-like protruding portion 20a is preferably arranged near the ring-like trimmed face 12, and preferably at least partially covers the ring-like trimmed face 12.

In this embodiment, the second member 1b has, at an end portion thereof opposite to the first member 1a in the central axis A1, a coupling portion 22 that is to be coupled with the rod 41. The coupling portion 22 has, at an end portion of the second member 1b opposite to the first member 1a, an opening C2, and the opening C2 receives the front end of the rod 41. More specifically, the coupling portion 22 of this embodiment is formed in the shape of a female screw, and the front end of the rod 41 is formed in the shape of a male screw. When the front end of the rod 41 is inserted and screwed into the coupling portion 22, the gasket 1 and the rod 41 are coupled.

Incidentally, the closer to the centroid of the gasket 1 the positions of the ring-like protruding portions 20a and 20b are, the more unlikely the central axis of the gasket 1 is to deviate from the central axis of the barrel 40, which allows the gasket 1 to reliably slide inside the barrel 40. Thus, especially in the case where an opening such as the opening C2 is formed in the second member 1b, and the centroid of the gasket 1 overlaps the first member 1a, the above-described configuration in which the ring-like protruding portion 20a at least partially covers the ring-like trimmed face 12 is preferable.

As described above, the second member 1b is connected to the first member 1a so as to cover the ring-like trimmed face 12 from the outer side in the radial direction. Thus, the ring-like trimmed face 12 is in contact with the inner wall of the second member 1b, and does not appear on the surface of the gasket 1. That is to say, the ring-like trimmed face 12 is not in contact with the inner circumferential face of the barrel 40, and thus even when variations appear in the outer circumferential dimensions of the ring-like trimmed face 12, the variations do not affect the performance of the gasket 1. Thus, even in the case of molding the first member 1a using the undercut method as described later, variations in the outer circumferential dimensions of the ring-like trimmed face 12 due to using the undercut method do not cause a problem.

Furthermore, the ring-like protruding portion 20a is formed on the second side circumferential face 21 so as to at least partially cover the ring-like trimmed face 12. As described above, the ring-like trimmed face 12 is recessed to be further inward in the radial direction than the portion of the first side circumferential face 11 other than the ring-like trimmed face 12, and thus the portion that covers the ring-like trimmed face 12 is thicker than in the case where the ring-like trimmed face 12 is not recessed (the ring-like trimmed face is not formed). As a result, the strength of the ring-like protruding portion 20a increases, and the gasket 1 is more firmly supported, and thus the central axis of the gasket 1 is more unlikely to deviate.

Furthermore, since the inert film 13 is not laminated on the ring-like trimmed face 12, the first member 1a and the second member 1b are connected to each other in a state in which the ring-like trimmed face 12 and the second member 1b are in direct contact with each other. Accordingly, the inert film 13 is between the ring-like trimmed face 12 and the second member 1b, peeling off of the second member 1b from the ring-like trimmed face 12 is prevented without reducing the connection force between the ring-like trimmed face 12 and the second member 1b. That is to say, the connection between the first member 1a and the second member 1b can be made more firm.

2. Method for Producing Syringe Gasket

Next, a method for producing the syringe gasket 1 according to this embodiment will be described with reference to FIGS. 4 to 6. In production of the gasket 1, first, a first mold 101 and a second mold 201 are prepared.

Figure 4:
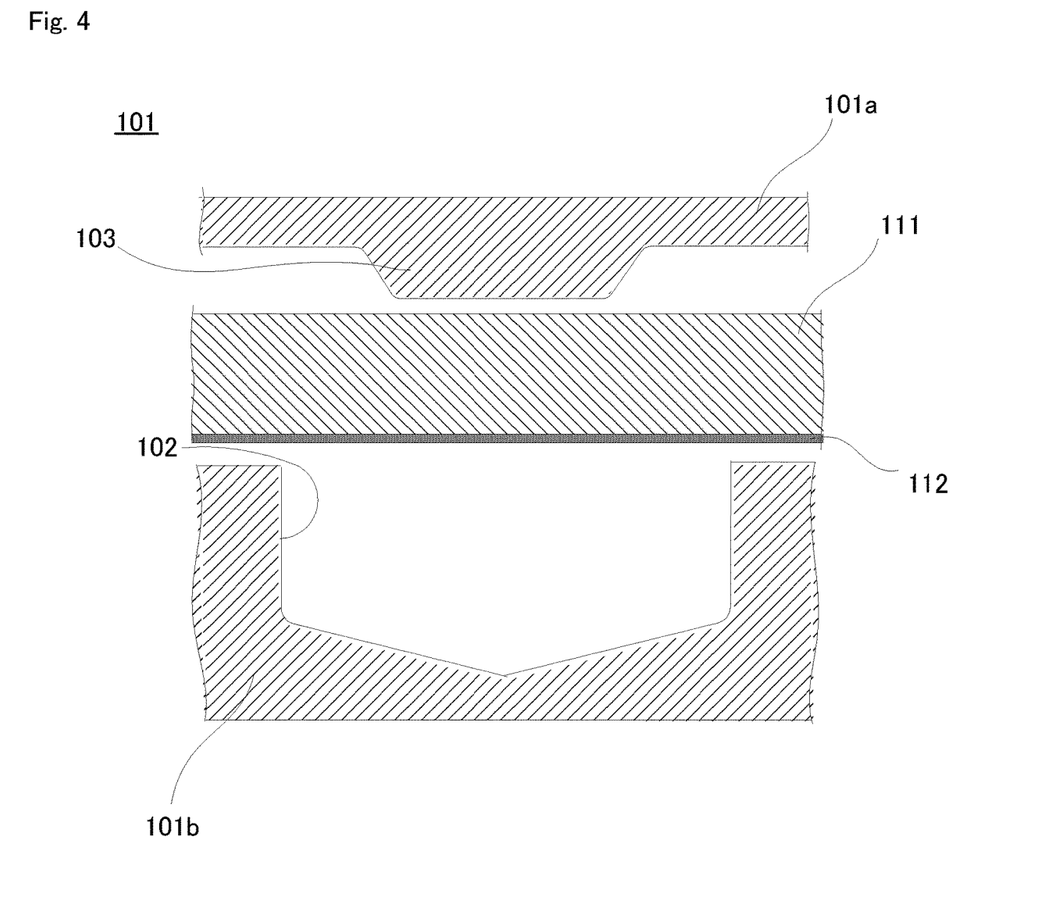
FIG. 4 is a schematic cross-sectional view showing a step of molding a first member of the syringe gasket according to an embodiment of the present invention.
Figure 5:
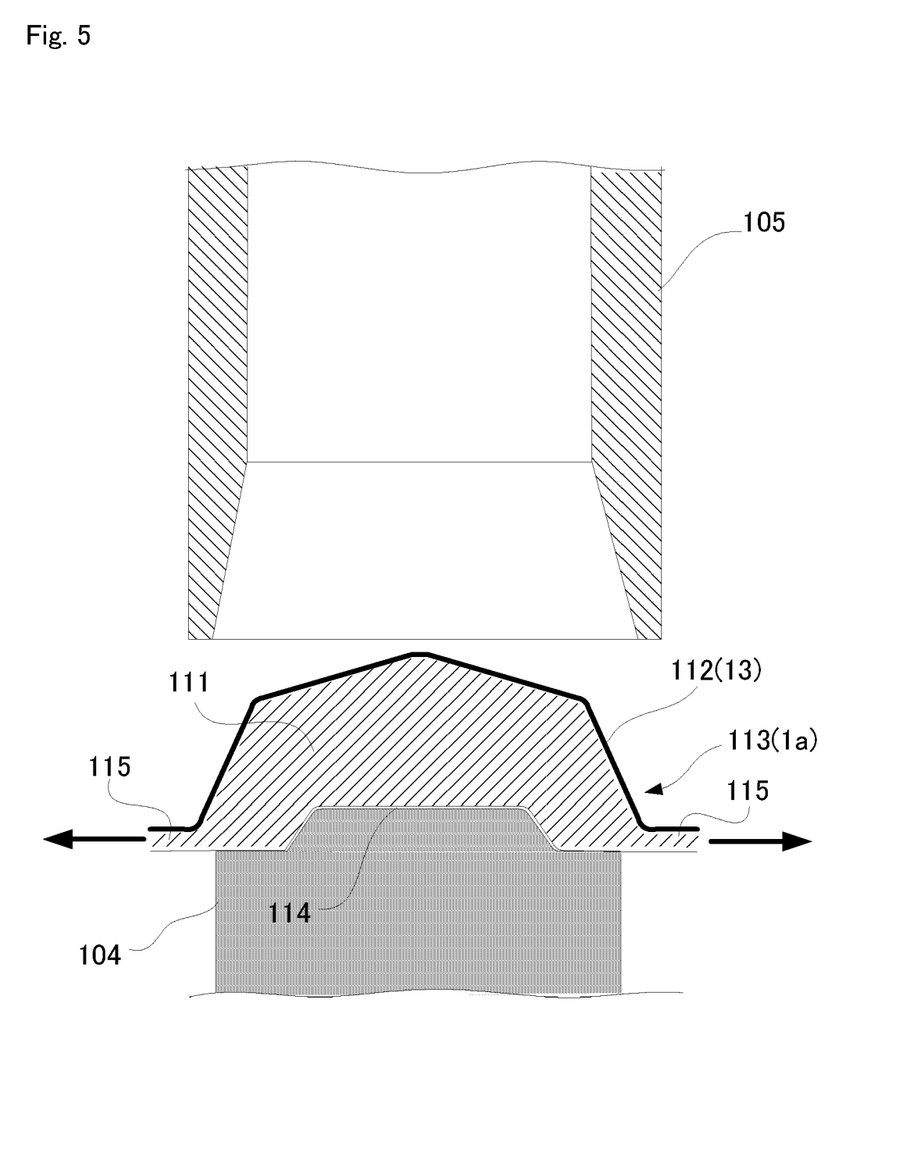
FIG. 5 is a schematic cross-sectional view showing a step of punching the first member of the syringe gasket according to an embodiment of the present invention.

FIG. 4 is a schematic cross-sectional view illustrating a step of molding the first member 1a. In this step, a first material 111 for forming the first member 1a and an inert film 112 for forming the inert film 13 are placed in the first mold 101 for molding the first member 1a. The first material 111 is made of rubber or a thermoplastic elastomer, and, in this embodiment, is in the shape of a sheet. If the first member 1a is made of rubber, the first material 111 may be a material obtained by mixing a vulcanizing agent and the like as appropriate with an unvulcanized rubber.

The first mold 101 includes an upper mold 101a and a lower mold 101b. A cavity 102 is formed in the face of the lower mold 101b facing the upper mold 101a, and the portion of the face other than the cavity 102 is substantially flat. The cavity 102 has a shape substantially corresponding to the external shape of the first member 1a, and its cross-section that is orthogonal to the depth direction is in the shape of a circle. That is to say, the cavity 102 is substantially in the shape of a solid cylinder, and, in this embodiment, the deepest portion in the shape of an inverted cone corresponds to the shape of the top face 10.

Meanwhile, a convex portion 103 in the shape of a circular truncated cone is formed on the face of the upper mold 101a facing the lower mold 101b, and the portion of the face other than the convex portion 103 is substantially flat. The convex portion 103 of the upper mold 101a is used in combination with the cavity 102 of the lower mold 101b. For the sake of simplicity, FIG. 4 shows only one cavity 102, but, in this embodiment, it is assumed that a plurality of cavities 102 arranged at predetermined intervals are formed in the lower mold 101b. Also, it is assumed that a plurality of convex portions 103 arranged at predetermined intervals so as to correspond to the cavities 102 of the lower mold 101b are formed on the upper mold 101a. The inert film 112 and the first material 111 are placed on the first mold 101 in an overlapping manner in the order of the inert film 112 and the first material 111 from the deeper side of the cavities 102.

In the subsequent step, the upper mold 101a and the lower mold 101b are closed to perform compression molding while applying heat to the inert film 112 and the first material 111. At this time, the central axis of the convex portion 103 of the upper mold 101a is positioned at the central axis of the cavity 102 of the lower mold 101b. Furthermore, at this time, the inert film 112 and the first material 111 are held between the upper mold 101a and the lower mold 101b and positioned within the cavity 102. If compression molding is performed in this state, the inert film 112 and the first material 111 are softened to fill the entire cavity 102 and molded into the shape of the cavity 102, and the inert film 112 and the first material 111 are joined together. Furthermore, if the first material 111 is an unvulcanized rubber, vulcanization is performed. Note that, as long as the first material 111 and the inert film 112 are joined together and the first material 111 and the inert film 112 are molded, the molding method is not limited to compression molding and other known methods may be used as appropriate.

Through the above-described processing, a first sheet 113 including a layer of the first material 111 and a layer of the inert film 112 (see FIG. 5) is obtained. The first sheet 113 is a sheet in which a plurality of first members 1a are coupled to each other at predetermined intervals corresponding to the above-described intervals of the cavities 102 of the lower mold 101b, and the first members 1a are coupled to each other at the bottom portions 14 thereof via coupling portions 115. The coupling portions 115 are formed by being held between the substantially flat portions of the face of the lower mold 101b facing the upper mold 101a excluding the cavities 102 and the substantially flat portions of the face of the upper mold 101a facing the lower mold 101b excluding the convex portions 103. Furthermore, concave portions 114 each substantially in the shape of a circular truncated cone corresponding to the convex portions 103 are formed in the first sheet 113 on the upper mold 101a side.

In the subsequent step, the first sheet 113 is cut to separate a plurality of first members 1a from the first sheet 113. Specifically, positioning rods 104 are respectively fitted to the concave portions 114 formed in the first sheet 113, and the first sheet 113 is fixed in this state. The positioning rods 104 are designed such that, when fitted to the concave portions 114 formed in the first sheet 113, a substantially uniform pulling force acts on the coupling portions 115 of the first sheet 113. The pulling force acts on the coupling portions 115 so as to pull the first members 1a included in the first sheet 113 outward in the radial direction, and the first members 1a spread out to be slightly flat. At this time, in each first member 1a included in the first sheet 113, mainly the portion corresponding to the bottom portion 14 spreads more, and the spread amount becomes smaller toward the top face 10. Thus, in this state, as shown in FIG. 5, the portion corresponding to the first side circumferential face 11 is substantially in the shape of a circular truncated cone that spreads outward from the top face 10 toward the bottom portion 14. Accordingly, if the first sheet 113 is punched in this state from the inert film 112 side using a punching blade 105, even considering variations in production, the punching blade 105 is not likely to come into contact with the portion of the first member 1a that is to be formed into the inert film 13. Thus, the first member 1a can be produced without damaging the inert film 13.

Subsequently, when the positioning rod 104 is removed from the concave portion 114 and the pulling force is canceled, a first member 1a in which the ring-like trimmed face 12 is formed along the outer circumference of the bottom portion 14 is obtained. Since the first sheet 113 is punched in a state where the coupling portion 115 is pulled in this manner, the punching blade 105 barely comes into contact with the layer of the inert film 112. When the pulling force is canceled, the ring-like trimmed face 12 that is the cut face formed as a result of the above-described punching returns to its original shape due to the elasticity thereof, and is recessed to be further inward in the radial direction than the other portions in the first side circumferential face 11 of the first member 1a.

Figure 6:
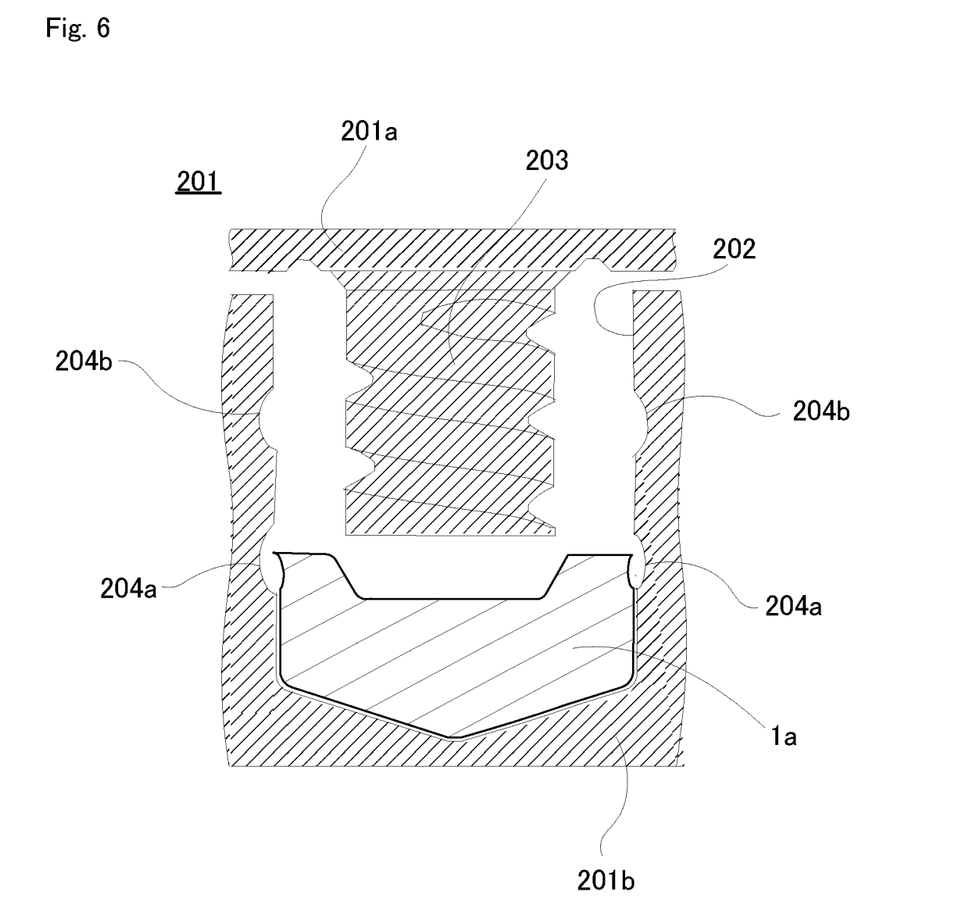
FIG. 6 is a schematic cross-sectional view showing a step of molding a second member of the syringe gasket according to an embodiment of the present invention.

In the subsequent step, the thus obtained first member 1a is placed in the second mold 201 as shown in FIG. 6. The second mold 201 includes an upper mold 201a and a lower mold 201b. A cavity 202 is formed in the face of the lower mold 201b facing the upper mold 201a, and the portion of the face other than the cavity 202 is substantially flat. The cavity 202 has a shape substantially corresponding to the external shape of the gasket 1, and its cross-section that is orthogonal to the depth direction is in the shape of a circle. That is to say, the cavity 202 is substantially in the shape of a solid cylinder, and, in this embodiment, the deepest portion is in a shape corresponding to the external shape of the first member 1a arranged upside down.

Meanwhile, a convex portion 203 in the shape of a circular truncated cone is formed on the face of the upper mold 201a facing the lower mold 201b, and the portion of the face other than the convex portion 203 is substantially flat. The convex portion 203 of the upper mold 201a is used in combination with the cavity 202 of the lower mold 201b. For the sake of simplicity, FIG. 6 shows only one cavity 202, but, in this embodiment, it is assumed that a plurality of cavities 202 arranged at predetermined intervals are formed in the lower mold 201b. Also, it is assumed that a plurality of convex portions 203 arranged at predetermined intervals so as to correspond to the cavities 202 of the lower mold 201b are formed on the upper mold 201a.

The first member 1a is placed in the cavity 202 of the second mold 201 such that the top face 10 is positioned on the deeper side. The portion of the cavity 202 on which the first member 1a is placed is formed such that the top face 10 and the first side circumferential face 11 are substantially fitted thereto.

In the subsequent step, the upper mold 201a and the lower mold 201b are closed, and the second material is poured onto the first member 1a inside the cavity 202. Accordingly, a second member 1b connected to the bottom portion 14 of the first member 1a, that is, a gasket 1 is molded. There is no particular limitation on the method for molding the second material, and known methods such as injection molding may be used. The second material is made of rubber or a thermoplastic elastomer. If the second member 1b is made of rubber, the second material may be a material obtained by mixing a vulcanizing agent and the like as appropriate with an unvulcanized rubber, and vulcanization is performed simultaneously with the step of molding the second material.

Ring-like concave portions 204a and 204b corresponding to the outer circumferential shapes of the ring-like protruding portions 20a and 20b are formed in the face constituting the side face of the cavity 202 in the lower mold 201b. The ring-like concave portion 204a is arranged on the deeper side relative to the ring-like concave portion 204b. The ring-like concave portion 204a is positioned so as to face the ring-like trimmed face 12 at the same depth as the ring-like trimmed face 12 when the first member 1a is placed at the deepest portion of the cavity 202. When such a second mold 201 is used, a second member in which the second material is in contact with the ring-like trimmed face 12 and the ring-like protruding portion 20a at least partially covers the ring-like trimmed face 12 is molded. The gasket 1 according to this embodiment is obtained by removing the gasket 1 from the second mold 201.

As described above, according to the method for producing the gasket 1 of this embodiment, the first sheet 113 including the first member 1a is first molded using the first mold 101, after which the first member 1a is cut through punching from the first sheet 113. It is possible to produce the first member 1a without damaging the inert film 112 of the first sheet 113 by causing a pulling force to act on a predetermined position on the first sheet 113 when cutting the gasket 1.

Furthermore, according to the method for producing the gasket 1 of this embodiment, in the step of molding the second member 1b while connecting it to the first member 1a using the second mold 201, the ring-like protruding portions 20a and 20b of the second member 1b are formed so as to cover the ring-like trimmed face 12 of the first member 1a. That is to say, the ring-like protruding portions 20a and 20b are molded using the molds, after which they are not punched as in the case of molding the first member 1a, and thus variations or errors that may appear in the outer circumferential dimensions of the ring-like protruding portions 20a and 20b can be reduced. Thus, the level of precision of the outer circumferential dimensions of the ring-like protruding portions 20a and 20b is improved, and the ring-like protruding portions 20a and 20b can support, with a uniform force along the circumferential direction, the gasket 1 inside the barrel 40, so that the central axis of the gasket 1 can be prevented from be deviating or shifting, and high liquid tightness can be realized.

3. Modified Examples

Although some embodiments of the present invention have been described above, the present invention is not limited to the foregoing embodiments, and variations that do not depart from the gist of the invention are possible. For example, the following variations are possible. Also, the substance of the following modifications can be combined as appropriate.

3-1

The coupling portion 22 may be in the shape of a male screw. In this case, the front end of the plunger rod 41 is in the shape of a female screw. Furthermore, the method for coupling the gasket 1 and the rod 41 is not limited to a screwing method. For example, it may be a snapping method in which the front end of the rod 41 is inserted and snapped into the opening C2 of the coupling portion 22.

3-2

The gasket 1 according to the foregoing embodiment can be produced using a method other than the production method according to the foregoing embodiment. Furthermore, the ring-like trimmed face 12 does not necessarily have to be a cut face formed using the undercut method. Furthermore, although an example of the undercut method was described in the process of the foregoing embodiment, but the specific methods are not limited thereto, and a method not using the positioning rod 104 may be employed.

3-3

Although a description was given in which two ring-like protruding portions 20a and 20b are arranged on the second side circumferential face 21, the number thereof may be one, or may be three or more. However, it is important that the ring-like protruding portion 20a that is the closest to the first member 1a at least partially covers the ring-like trimmed face 12.

Reference Signs List

1 Syringe gasket
1a First member
1b Second member
10 Top face
11 First side circumferential face
12 Ring-like trimmed face
13 Inert film
14 Bottom portion
20a, 20b Ring-like protruding portion
21 Second side circumferential face
101 First mold
102 Cavity of first mold
103 Convex portion
104 Positioning rod
105 Punching blade
111 First material
112 Inert film
113 First sheet
114 Concave portion
201 Second mold
202 Cavity of second mold

The invention claimed is:

1. A syringe gasket configured to be coupled to a plunger rod of a syringe, and to slide inside a barrel of the syringe by being pushed with the plunger rod, comprising:
a first member configured to be inserted into the barrel, and to be in contact with a liquid accommodated in the barrel; and
a second member configured to be inserted into the barrel, and to be coupled to the plunger rod, the second member being connected to the first member,
wherein
the first member includes:
a top face configured to be in contact with the liquid; and
a first side circumferential face that is continuous with an outer circumferential edge of the top face, and configured to face an inner circumferential face of the barrel,
the first side circumferential face has, at an end portion thereof close to the second member, a ring-shaped trimmed face, and the ring-shaped trimmed face is recessed to be closer to the inner side in a radial direction than the portion of the first side circumferential face other than the ring-shaped trimmed face,
an inert film is laminated on the top face and the portion of the first side circumferential face other than the ring-shaped trimmed face,
the second member includes:
a second side circumferential face configured to face the inner circumferential face of the barrel; and
a ring-shaped protruding portion that extends in a circumferential direction on the second side circumferential face, projects outward in the radial direction from the second side circumferential face, and is configured to be contact with the inner circumferential face of the barrel when the second member is inserted into the barrel, and
the ring-shaped protruding portion at least partially covers the ring-shaped trimmed face from the outer side in the radial direction.

2. The syringe gasket according to claim 1, wherein the ring-shaped protruding portion covers the entire ring-shaped trimmed face from the outer side in the radial direction.

3. The syringe gasket according to claim 1, wherein the first member and the second member are made of a rubber or a thermoplastic elastomer.

4. The syringe gasket according to claim 2, wherein the first member and the second member are made of a rubber or a thermoplastic elastomer.

5. The syringe gasket according to claim 1, wherein the top face has a convex portion projecting toward a space in which the liquid is accommodated in the barrel.

6. The syringe gasket according to claim 2, wherein the top face has a convex portion projecting toward a space in which the liquid is accommodated in the barrel.

7. The syringe gasket according to claim 1, wherein the top face has, at an outer circumferential portion thereof, an inclined face that is inclined toward the second member as being closer to the outer side in the radial direction.

8. The syringe gasket according to claim 2, wherein the top face has, at an outer circumferential portion thereof, an inclined face that is inclined toward the second member as being closer to the outer side in the radial direction.

9. The syringe gasket according to claim 7, wherein an angle formed by the portion of the first side circumferential face other than the ring-shaped trimmed face and the inclined face is 90° or more and 110° or less.

10. The syringe gasket according to claim 8, wherein an angle formed by the portion of the first side circumferential face other than the ring-shaped trimmed face and the inclined face is 90° or more and 110° or less.

11. The syringe gasket according to claim 1, wherein the inert film is made of a material selected from the group consisting of tetrafluoroethylene-ethylene copolymer, modified tetrafluoroethylene-ethylene copolymer, and polychlorotrifluoroethylene.

12. The syringe gasket according to claim 2, wherein the inert film is made of a material selected from the group consisting of tetrafluoroethylene-ethylene copolymer, modified tetrafluoroethylene-ethylene copolymer, and polychlorotrifluoroethylene.

13. A method for producing a syringe gasket configured to be coupled to a plunger rod of a syringe, and to slide inside a barrel of the syringe by being pushed with the plunger rod, comprising:
   placing in an overlapping manner a first material that is a material of a rubber or a thermoplastic elastomer and an inert film, in a cavity of a first mold, such that the inert film is positioned on the deeper side;
   molding a first sheet including a layer of the inert film and a layer of the first material, by molding the first material and the inert film together in the cavity of the first mold;
   punching a predetermined portion of the first sheet from the inert film side while causing a pulling force to act on the first sheet, thereby obtaining a first member in which the inert film is laminated on a top face and a side circumferential face thereof and a ring-shaped trimmed face is formed on a bottom portion opposite to the top face;
   placing the first member in a cavity of a second mold such that the top face is positioned on the deeper side;
   molding a second member connected to the bottom portion of the first member, by pouring a second material that is a material of a rubber or a thermoplastic elastomer on the first member in the cavity of the second mold in which the first member has been placed; and
   removing the syringe gasket including the first member and the second member from the second mold;
   wherein molding the second member includes pouring the second material such that the second material is in contact with the ring-shaped trimmed face of the first member, and a ring like ring-shaped protruding portion that at least partially covers the ring-shaped trimmed face is formed.

* * * * *